United States Patent [19]

Kiefer

[11] 4,309,186

[45] Jan. 5, 1982

[54] HYDROPHILIC FILM FOR DETECTION OF HEAVY METALS

[75] Inventor: John E. Kiefer, Kingsport, Tenn.

[73] Assignee: Eastman Kodak Company, Rochester, N.Y.

[21] Appl. No.: 164,371

[22] Filed: Jun. 30, 1980

[51] Int. Cl.³ .................. C08L 1/12; G01N 21/78; G01N 33/20
[52] U.S. Cl. .................. 23/230 R; 106/194; 252/408; 264/216; 422/56
[58] Field of Search .......... 23/230 R; 422/56, 57, 422/55; 106/169, 193 M, 193 J, 198, 194; 264/216; 252/408

[56] References Cited

U.S. PATENT DOCUMENTS

| | | | |
|---|---|---|---|
| 3,560,232 | 2/1971 | Littman | 106/169 |
| 3,607,093 | 9/1971 | Stone | 422/56 |
| 3,635,679 | 1/1972 | Bloch et al. | 23/230 |
| 3,661,532 | 5/1972 | Schmitt et al. | 422/56 |
| 3,666,508 | 5/1972 | Justice et al. | 106/169 X |
| 4,050,898 | 9/1977 | Goffe et al. | 422/57 |

Primary Examiner—Arnold Turk
Attorney, Agent, or Firm—Malcolm G. Dunn; Daniel B. Reece, III

[57] ABSTRACT

A transparent hydrophilic film for detecting the presence of heavy metals in aqueous solutions; the method of making same and the film as made by the method; and the use of a transparent hydrophilic film having therein a dispersion of finely precipitated zinc sulfide which becomes discolored by ion exchange when indicating the presence of heavy metals, the degree of discoloration being also a measurement of the concentration of such heavy metals.

23 Claims, 1 Drawing Figure

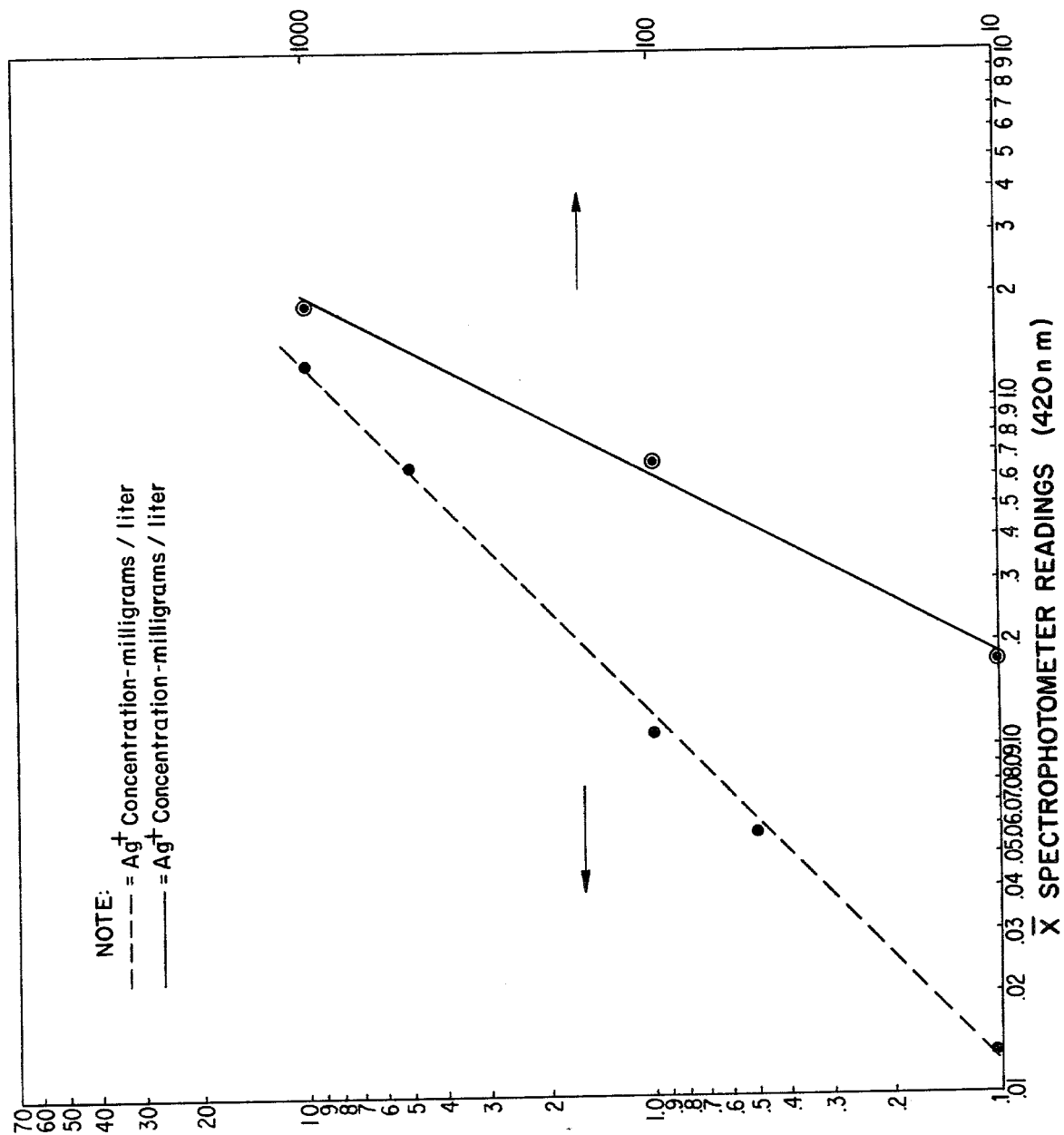

HYDROPHILIC FILM FOR DETECTION OF HEAVY METALS

TECHNICAL FIELD

My invention is directed to a transparent hydrophilic film for the detection of heavy metals in aqueous solutions such as the detection of how much silver is present in a photographic solution; to the use of such film; and to the method for making such film.

DESCRIPTION OF PRIOR ART

The Bannigan patent, U.S. Pat. No. 3,282,650, discloses an ion indicating device which indicates the presence of ions in the effluent of ion exchange processes. The device comprises an ion-sensitive device made from resilient strip or sheet material and having secured to one side thereof a strip or sheet of active ion-exchange material. The device in its operation makes use of the volume change characteristics such as by swelling or shrinking, according to the nature of the ion the device has absorbed. Deformation of the device will occur when the device is contacted with an ionized solution.

An object of the present invention, however, is to provide a transparent hydrophilic film that will show a color change when detecting the presence of heavy metals in aqueous solutions.

For instance there are several silver-estimating test papers available that are used by photo processors to approximate the amount of silver in photographic recovery systems and to adjust the fixer replenisher rate to obtain maximum fixer efficiency. These test papers are efficient down to a concentration of 1000 ppm. (parts per million) silver in aqueous solutions. There is, however, a need for a test medium capable of detecting silver at about 0.5 ppm. Also, any test developed for detecting such silver concentrate must be relatively simple and must employ instrumentation readily available to photo processors.

Another object of this invention, therefore, is to provide a transparent hydrophilic film that will detect in aqueous solutions at least 0.5 ppm. (part per million), and preferably about 0.1 ppm., of the presence of heavy metals such as silver, bismuth, copper, lead, mercury and gold.

Still another object of the invention is to use a transparent hydrophilic film as an analytical device for determining the presence and the concentration of heavy metal in an aqueous solution.

A further object of the invention is to provide a method for making a transparent hydrophilic film that will detect the presence of heavy metals in aqueous solutions.

A still further object of the invention is to provide a transparent hydrophilic film, as made by the method, for detecting the presence of heavy metals in aqueous solutions.

Other objects of the invention will become apparent to those skilled in the art to which this invention pertains from the disclosure to follow.

DISCLOSURE OF INVENTION

The invention is directed to a transparent hydrophilic film that becomes discolored when detecting the presence of heavy metals in aqueous solutions, to a method of making a transparent hydrophilic film for detecting heavy metals, to a hydrophilic film as made by the method, and to the use of a transparent hydrophilic film which becomes discolored when indicating the presence of heavy metals, the degree of discoloration being also a measurement of the concentration of such heavy metals.

The method includes dissolving zinc chloride and a cellulose ester in a volatile solvent to form a liquid solution, casting the liquid solution to form a film, and then treating the film with a water soluble sulfide salt in an aqueous solution to convert the zinc chloride to a transparent dispersion of finely precipitated zinc sulfide in the film.

The cellulose ester may be selected from cellulose acetate, cellulose butyrate, cellulose propionate, and mixed esters thereof.

The water soluble sulfide salt may be selected from sodium sulfide, ammonium sulfide and potassium sulfide, and may comprise about 1% to a saturated solution in the aqueous solution, and preferably about 5% to a saturated solution in the aqueous solution. A saturated solution contains about 16% of the water soluble salt. Alternately, an organic sulfide donor such as thioacetamide may be used to convert the zinc chloride to zinc sulfide.

The solvent may be selected from acetone and methylene chloride containing about 10% methanol.

The transparent hydrophilic film, after such treatment, may comprise about 2 to about 40% by weight zinc sulfide and preferably about 2 to about 10% by weight zinc sulfide.

BRIEF DESCRIPTION OF DRAWING

FIG. 1 is a graph showing a representation of the relation of silver concentration in the film to the reflectance density value determined as described herein.

BEST MODE FOR CARRYING OUT THE INVENTION

As mentioned above, the invention disclosed herein, therefore, concerns a method of making a transparent film for detecting heavy metals; the product of the method, since all of the resulting characteristics of the films as treated may not be known and therefore not completely definable in a product claim per se; a hydrophilic transparent film for detecting metals; and the use of a transparent film having a dispersion of finely precipitated zinc sulfide therein for indicating the presence and concentration of heavy metals in aqueous solutions when such aqueous solutions contact the film.

The film resulting from practice of this invention may serve as a field test kit for measuring, for instance, dilute silver concentration in photographic solutions. This film, as tested, has been found capable of detecting as low as 0.1 part per million (ppm.) of silver in a photographic solution. The film undergoes a detectable color change or discoloration when exposed to aqueous solutions containing silver.

Some other heavy metals that may also be detected by the film include bismuth, copper, lead, mercury and gold.

The film is formed from a cellulose ester and zinc chloride by dissolving the two in a volatile solvent to form a liquid solution. The liquid solution is cast into a film, and the film is then treated with a water soluble sulfide salt in an aqueous solution so as to convert the zinc chloride to zinc sulfide. The converted zinc sulfide is water insoluble and becomes dispersed as a fine precipitation within the film. The resulting film, therefore, is hydrophilic and is essentially transparent.

When using the film in an aqueous solution containing a particular heavy metal, the film becomes discolored as a result of an ion exchange reaction between the zinc sulfide and the heavy metal.

The cellulose ester employed must be soluble in a volatile organic solvent and must be compatible with zinc chloride in solution. The cellulose ester may be selected from cellulose acetate, cellulose butyrate, cellulose propionate and mixed esters thereof.

The water soluble sulfide salt may be selected, preferably, from sodium sulfide, ammonium sulfide and potassium sulfide for the purpose of converting the zinc chloride to a water insoluble zinc sulfide. Alternately, an organic sulfide donor such as thioacetamide may be used to convert the zinc chloride to zinc sulfide. The chloride washes out. The water soluble salt may comprise about 1% to a saturated solution in an aqueous solution, and preferably may comprise about 5% to a saturated solution in such aqueous solution. As previously indicated, a saturated solution contains about 16% of the water soluble salt. The water soluble salt is a strong base and may saponify the cellulose ester to form cellulose. The saponification, however, does not impair the desirable properties of the product. The base of the cellulose ester film may thus be at least partially saponified, depending upon, for instance, the amount of water soluble sulfide salt in the aqueous solution used to treat the film and the length of treatment time.

The film, after treatment with the sulfide salt, must be hydrophilic.

The solvent for dissolving zinc chloride and cellulose ester must be a volatile one in order that a film may be cast or formed upon evaporation of the solvent. Preferred solvents include acetone and methylene chloride containing about 10% methanol. Other volatile solvents that may be used include other esters, ketones and chlorinated hydrocarbons commonly used to dissolve the particular cellulose ester of concern.

The water insoluble, dispersed, finely precipitated zinc sulfide in the treated film may comprise about 2 to about 40% by weight, and preferably about 2 to about 10% by weight.

What is unexpected in this invention is that when zinc sulfide is formed in the film in the manner taught herein, a clear film is obtained. For instance, heavy metal sulfide salts, other than zinc, will form colored or nonuniform films. If an attempt were made initially to form a film from zinc sulfide and cellulose ester, the resulting film would be white and heterogeneous and thus not suitable for the use described herein.

As heretofore mentioned, there are several silver estimating test papers on the market that are used by photoprocessors to approximate the concentration of silver in photographic recovery systems, and to adjust the fixer replenisher rate to obtain maximum fixer efficiency. These estimating test papers, however, appear to be efficient only as low as to a concentration of 1000 parts per million (ppm.) silver in aqueous solutions.

There is a need, however, to be able to be much more efficient and more sensitive in detecting far lower concentrations of heavy metals in aqueous solutions, and especially, also, from the standpoint of ecological concerns before discharging such aqueous solutions. The practice of this invention, therefore, results in a significant improvement over these known silver estimating test papers, and as also previously mentioned herein, will be capable of detecting in aqueous solutions as low as 0.1 part per million (ppm.) silver, for instance, in a photographic solution.

EXPERIMENTS

In the first experiments, somewhat crude by comparison with the more sophisticated ones conducted later, test films were cast from an acetone solution containing two parts cellulose acetate filter tow and one part zinc chloride. The dry films had a thickness of 33 microns (1.3 mils). One-half inch squares of the film were treated with a 16% sodium sulfide solution (made by dissolving the sodium sulfide in distilled water) for 20 minutes at room temperature, water washed, and air dried. The films were then exposed by dipping them in photographic fixer solutions containing, respectively, 0, 0.5, 5, 50, 500 and 5000 parts per million silver ion ($Ag^+$) (AgCl solutions) for 45 minutes. After washing the exposed films in distilled water, the color of the dry films ranged from clear to black as a result of the different ion exchanges taking place in which the silver replaced the zinc in the films to different extents, depending upon the amount of concentration of the silver ion ($Ag^+$) in the solution. Table 1 below shows the results of these early experiments when a visual comparison was made of the different samples.

TABLE 1

| | Test Film for Silver Analysis | | |
|---|---|---|---|
| Film No. | % $ZnCl_2$[a] | Treatment with AgCl Solution Milligrams $Ag^{30}$/Liter[b] | Film Color |
| 1 | 50 | 0.0 | Clear |
| 2 | 50 | 0.5 | Light Yellow |
| 3 | 50 | 5.0 | Yellow |
| 4 | 50 | 50.0 | Yellow-Brown |
| 5 | 50 | 500.0 | Black |
| 6 | 50 | 5000.0 | Black |

[a]Based on cellulose acetate weight
[b]Dilute photographic fixer solution containing AgCl The following, more sophisticated, experiments were conducted for the purpose of testing the efficiency of the film detector.

Four dopes were prepared, consisting of

1. Four parts of cellulose acetate extrusion-coating type powder and one part zinc chloride were dissolved in acetone. The cellulose acetate had an average acetyl content of about 39.9%; a hydroxyl content of about 3.2%; a combined acetic acid content of about 55.7%; as determined by the procedure of ASTM D-871-63; a falling ball viscosity of about 25 seconds at about 95.0 poises as determined by the procedure in ASTM D-817-65 (Formula A) and D-1343-56; a melting point range of about 240° C. to about 260° C.; and a glass transition temperature (Tg) of about 184° C.

2. Twenty parts cellulose acetate (same cellulose acetate as in Item 1) and one part zinc chloride were dissolved in acetone.

3. Four parts cellulose acetate (same cellulose acetate as in Item 1) and one part zinc chloride were dissolved in 9:1 methylene chloridemethanol.

4. Twenty parts cellulose acetate (same cellulose acetate as in Item 1) and one part zinc chloride were dissolved in 9:1 methylene chloridemethanol.

Separate dopes were then made from the mixtures in Items 1 through 4, and films were made from the dopes by casting the dopes onto glass plates using a Gardner film casting knife (manufactured by Gardner Laboratories, Inc., Bethesda, Maryland).

A 16% sodium sulfide solution was used to treat the films, the solution being made by dissolving the sodium sulfide in distilled water.

The photographic fixer solution containing silver ion ($Ag^+$) was prepared as follows: Silver chloride (5.05 grams) was dissolved in one gallon of a photographic fixer solution using distilled water. This then represented a concentration of one gram of silver ion ($Ag^+$) per liter of solution. Aliquots of this solution were then diluted with distilled water to prepare dilute silver ion ($Ag^+$) solutions as low as 0.1 milligram silver ion ($Ag^+$) per liter.

The resulting tests revealed that mixtures of cellulose acetate-zinc chloride dissolved in 9:1 methylene chloridemethanol solution produced films having superior clarity and smoothness to films made from acetone solutions.

These more sophisticated experiments were designed to study the effects of (1) varying the levels of cellulose acetate-zinc chloride, and (2) the concentration, temperature, and time effects of sodium sulfide solutions on film clarity.

These tests revealed that films made from dopes with 20-parts cellulose acetate plus 1 part zinc chloride (5% based on cellulose acetate weight) and then treated with 16% sodium sulfide for two minutes at room temperature produced films having the clarity and smoothness necessary for the silver test kits.

The films shown in Table 2 below were cast to a dry thickness of 1.5–1.7 mils. The cellulose acetate powder used was a coating-extrusion type material.

Sample film pieces measuring 1 inch × 6 inches were immersed in 16% sodium sulfide for two minutes at room temperature, washed in distilled water and air dried. One-inch squares of the film were treated with AgCl in photographic fixer solution which contained 0.1 milligram to 1 gram $Ag^+$/liter. After washing the films with distilled water, they were air dried and evaluated for the amount of color pick-up due to the amount of $Ag^+$ (silver ions) deposited in the film.

One method for evaluating the film, is, of course, by visual inspection as shown by Table 1 above.

A second method involves use of a spectrophotometer.

In reference to FIG. 1, the reflectance density data shown therein was obtained on a spectrophotometer instrument constructed in the following manner: Light from three 75 watt tungsten lamps, positioned at 120° with respect to each other, was focused through a Pyrex glass window on the film sample at an angle of 45°. A NBS (National Bureau of Standards) white glass tile was positioned behind the film sample. The diffusely reflected light emitted perpendicular to the sample plane was collected by a mirror and focused on the entrance slit (two nanometers) of a Farrand Foci-Flex monochromator. Emission from the monochromator was detected and its intensity determined with a blank substract photomultiplier microphotometer by means of a 1P28 photomultiplier tube (American Instrument Company). Data were expressed as reflectance density.

The instrument is calibrated by using the NBS white glass tile as the reflectance standard, and a black felt was used as the zero reflectance standard.

This instrument measures the amount of light diffusely reflected by the sample film at a wave length of 420 nanometers (nm). The measurements from this test are shown in Table 2 below. The data points were averaged ($\overline{X}$) from four sets of film containing five concentrations of silver and plotted on the graph in FIG. 1. The broken line plot represents the data acquired from the films treated for one hour with 100 milliliters of 0.1–10 milligrams $Ag^+$/liter of dilute fixer solution. The ordinate for the broken line plot is to be read from the left, as indicated by the directional arrow. The colors ranged from a very pale tint (0.1 ppm. $Ag^+$) to a medium brown color (10 ppm. $Ag^+$). The solid line plot represents the data acquired from the films treated for five minutes with 100 milliters of 10 and 100 ppm. $Ag^+$/liter of dilute fixer solution and 1000 ppm. $Ag^+$/liter of concentrated fixer solution. The ordinate for the solid line plot is to be read from the right, as indicated by the directional arrow. The colors ranged from light brown (10 ppm. $Ag^+$) to dark brown (1000 ppm. $Ag^+$).

TABLE 2

Evaluation of Film for Silver Test Kits

| Film No. | % $ZnCl_2$[a] | Solvent Used[c] To Cast Film | Treatment with $Na_2S$ | | Treatment with AgCl Solution Milligrams $Ag^+$/Liter[b] | Spectrophotometer Analysis, 420 nm ($\overline{X}$) |
|---|---|---|---|---|---|---|
| | | | % $Na_2S$ | Solution Time | | |
| 1 | 5 | d | 16 | 2 min. | 0.1 | 0.014 |
| 2 | 5 | d | 16 | 2 min. | 1.0 | 0.154 |
| 3 | 5 | d | 16 | 2 min. | 10.0 | 0.760 |
| 4 | 25 | d | 16 | 2 min. | 0.1 | * |
| 5 | 25 | d | 16 | 2 min. | 1.0 | * |
| 6 | 25 | d | 16 | 2 min. | 10.0 | * |
| 7 | 5 | e | 16 | 2 min. | 0.1 | 0.018 |
| 8 | 5 | e | 16 | 2 min. | 1.0 | 0.162 |
| 9 | 5 | e | 16 | 2 min. | 10.0 | 1.492 |
| 10 | 25 | e | 16 | 2 min. | 0.1 | 0.034 |
| 11 | 25 | e | 16 | 2 min. | 1.0 | 0.154 |
| 12 | 25 | e | 16 | 2 min. | 10.0 | 1.580 |
| 13 | 5 | e | 16 | 2 min. | 10.0 | 0.176 |
| 14 | 5 | e | 16 | 2 min. | 100.0 | 0.663 |
| 15 | 5 | e | 16 | 2 min. | 1000.0 | 1.800 |
| 16 | 5 | e | 16 | 2 min. | 0.1 | 0.011 |
| 17 | 5 | e | 16 | 2 min. | 0.5 | 0.040 |
| 18 | 5 | e | 16 | 2 min. | 1.0 | 0.034 |
| 19 | 5 | e | 16 | 2 min. | 5.0 | 0.608 |
| 20 | 5 | e | 16 | 2 min. | 10.0 | 1.210 |
| 21 | 5 | e | 16 | 2 min. | 0.1 | 0.015 |

TABLE 2-continued

| | | | Evaluation of Film for Silver Test Kits | | | |
| | | | Treatment with Na$_2$S | | Treatment with | |
| Film No. | % ZnCl$_2$[a] | Solvent Used[c] To Cast Film | % Na$_2$S | Solution Time | AgCl Solution Milligrams Ag$^+$/Liter[b] | Spectrophotometer Analysis, 420 nm ($\overline{X}$) |
|---|---|---|---|---|---|---|
| 22 | 5 | e | 16 | 2 min. | 0.5 | 0.058 |
| 23 | 5 | e | 16 | 2 min. | 1.0 | 0.082 |
| 24 | 5 | e | 16 | 2 min. | 5.0 | 0.533 |
| 25 | 5 | e | 16 | 2 min. | 10.0 | 0.868 |
| 26 | 5 | e | 16 | 2 min. | 0.1 | 0.007 |
| 27 | 5 | e | 16 | 2 min. | 0.5 | 0.074 |
| 28 | 5 | e | 16 | 2 min. | 1.0 | 0.198 |
| 29 | 5 | e | 16 | 2 min. | 5.0 | 0.675 |
| 30 | 5 | e | 16 | 2 min. | 10.0 | 0.815 |
| 31 | 5 | e | 16 | 2 min. | 0.1 | 0.012 |
| 32 | 5 | e | 16 | 2 min. | 0.5 | 0.061 |
| 33 | 5 | e | 16 | 2 min. | 1.0 | 0.078 |
| 34 | 5 | e | 16 | 2 min. | 5.0 | 0.753 |
| 35 | 5 | e | 16 | 2 min. | 10.0 | 1.758 |

[a] Based on cellulose acetate weight
[b] AgCl in photographic fixer solution
[c] Films cast from acetone were slightly hazy, grainy and badly rippled
[d] Acetone
[e] 9:1 methylene chloride - methanol

FURTHER EXAMPLES

The following examples demonstrate that cellulose esters other than cellulose acetate can be used in carrying out this invention. The following films are made from 20 parts cellulose ester and one part zinc chloride. A 9:1 mixture of methylene chloride-methanol is used as the casting solvent. These cellulose esters are:

cellulose tripropionate
cellulose acetate propionate (Eastman CAP 141, a product of Eastman Chemical Products, Inc.)
cellulose tributyrate
cellulose acetate butyrate (Eastman CAB 171-25, a product of Eastman Chemical Products, Inc.)

Each film is treated with a 15% ammonium sulfide solution for 15 minutes, then water washed and dried. Each of the films turns black when dipped into a 0.5% solution of silver nitrate, cupric acetate, lead acetate or mercuric acetate.

From the disclosure herein it should now be apparent depending upon the concentration of the silver sulfide deposited on the film surface, that it is possible to fabricate color charts to be used as field test kits for estimating dilute silver concentration in photographic solutions.

The invention has been described in detail with particular reference to certain preferred embodiments thereof, but it will be understood that variations and modifications can be effected within the spirit and scope of the invention.

I claim:

1. The method of making a transparent hydrophilic film for detecting heavy metals, comprising dissolving zinc chloride and a cellulose ester in a volatile solvent to form a liquid solution, casting said liquid solution to form a film, and then treating the film with a sulfide donor to convert said zinc chloride to a transparent dispersion of finely precipitated zinc sulfide.

2. The method as defined in claim 1, wherein said cellulose ester is selected from the group consisting of cellulose acetate, cellulose butyrate, cellulose propionate and mixed esters thereof.

3. The method as defined in claim 1, wherein said sulfide donor is selected from sodium sulfide, ammonium sulfide or potassium sulfide.

4. The method as defined in claim 1, wherein said solvent is selected from acetone and methylene chloride containing about 10% methanol.

5. The method according to claim 1, wherein said film comprises about 2 to about 40% by weight zinc sulfide.

6. The method according to claim 1, wherein said film comprises about 2 to about 10% by weight zinc sulfide.

7. The method according to claim 1, wherein said sulfide donor comprises about 1% to a saturated solution in said aqueous solution for treating said film.

8. The method according to claim 1, wherein said sulfide donor comprises about 5% to a saturated solution in said aqueous solution for treating said film.

9. A transparent hydrophilic film for detecting heavy metals and made in accordance with the method defined in claim 1.

10. A transparent hydrophilic film and made in accordance with the method defined in claim 7.

11. A transparent hydrophilic film and made in accordance with the method defined in claim 8.

12. A hydrophilic film for detecting heavy metals, comprising a film having a dispersion therein of finely precipitated zinc sulfide, the resulting film being transparent.

13. A hydrophilic film as defined in claim 12, wherein the base of said film includes a cellulose ester.

14. A hydrophilic film as defined in claim 13, wherein said cellulose ester is selected from the group consisting of cellulose acetate, cellulose butyrate, cellulose propionate and mixed esters thereof.

15. A hydrophilic film as defined in claim 14, wherein said cellulose ester is at least partially saponified.

16. A hydrophilic film as defined in claim 12, wherein said film comprises about 2 to about 40% by weight zinc sulfide.

17. A hydrophilic film as defined in claim 12, wherein said film comprises about 2 to about 10% by weight zinc sulfide.

18. In a method of detecting heavy metals in an aqueous solution wherein said aqueous solution contacts a film for indicating the presence of said heavy metals, the improvement comprising using a film having a dispersion of finely precipitated zinc sulfide therein, said film being transparent and becoming discolored when indicating the presence of heavy metals, the extent of such discoloration also indicating the measurement of concentration of such heavy metals.

19. In a method as defined in claim 18, wherein said transparent film is hydrophilic and has a film base of a cellulose ester.

20. In a method as defined in claim 19, wherein said cellulose ester is selected from the group consisting of cellulose acetate, cellulose butyrate, cellulose propionate and mixed esters thereof.

21. In a method as defined in claim 20, wherein said cellulose ester is at least partially saponified.

22. In a method as defined in claim 18, wherein said film comprises about 2 to about 40% by weight zinc sulfide.

23. In a method as defined in claim 18, wherein said film comprises about 2 to about 10% by weight zinc sulfide.

* * * * *